(12) United States Patent
Black (10) Patent No.: US 10,149,707 B2
(45) Date of Patent: Dec. 11, 2018

(54) BONE FIXATION PLATE SYSTEM AND METHOD

(75) Inventor: Michael Black, Swarthmore, PA (US)

(73) Assignee: Globus Medical, Inc., Audubon, PA (US)

( * ) Notice: Subject to any disclaimer, the term of this patent is extended or adjusted under 35 U.S.C. 154(b) by 539 days.

(21) Appl. No.: 13/211,761

(22) Filed: Aug. 17, 2011

(65) Prior Publication Data

US 2013/0046348 A1   Feb. 21, 2013

(51) Int. Cl.
*A61B 17/80* (2006.01)

(52) U.S. Cl.
CPC ...... *A61B 17/8042* (2013.01); *A61B 17/8047* (2013.01); *A61B 17/8052* (2013.01)

(58) Field of Classification Search
CPC .. A61B 17/8033; A61B 17/8052; A61B 17/80
USPC ............... 606/70–71, 280–299; 411/353
See application file for complete search history.

(56) References Cited

U.S. PATENT DOCUMENTS

| | | | | |
|---|---|---|---|---|
| 6,030,389 | A * | 2/2000 | Wagner | A61B 17/7059 606/246 |
| 6,723,098 | B1 * | 4/2004 | Shah | 606/71 |
| 2001/0037112 | A1 * | 11/2001 | Brace | A61B 17/8038 606/86 B |
| 2002/0151899 | A1 * | 10/2002 | Bailey et al. | 606/69 |
| 2007/0162019 | A1 * | 7/2007 | Burns | A61B 17/8047 606/281 |
| 2008/0177330 | A1 * | 7/2008 | Ralph | A61B 17/8038 606/290 |
| 2008/0306550 | A1 * | 12/2008 | Matityahu | 606/290 |
| 2009/0054930 | A1 * | 2/2009 | Aflatoon | 606/246 |
| 2009/0062862 | A1 * | 3/2009 | Perrow et al. | 606/280 |
| 2009/0312803 | A1 * | 12/2009 | Austin et al. | 606/305 |
| 2009/0318978 | A1 * | 12/2009 | Podgorski | A61B 17/7059 606/290 |
| 2010/0160973 | A1 * | 6/2010 | Leung | 606/289 |
| 2010/0234897 | A1 * | 9/2010 | Fisher | A61B 17/8042 606/286 |
| 2011/0230885 | A1 * | 9/2011 | Weiner | A61B 17/8009 606/71 |

FOREIGN PATENT DOCUMENTS

WO   WO 2004/071276 A2 *   8/2004

* cited by examiner

*Primary Examiner* — Zade Coley
*Assistant Examiner* — Jessica Weiss (57) ABSTRACT

A fastener, for example a bone screw, is sized to pass through a hole of an implant, for example a bone plate, the fastener having a shaft or anchor portion engageable with body tissue, and a head portion. A locking cap secures to the bone plate and covers the head to block the head and inhibit screw back out. Alternatively or additionally, a locking disc located in the plate hole resiliently deflects downward to allow screw insertion, but is blocked to limit or prevent upward deflection so that screw back out is inhibited.

11 Claims, 6 Drawing Sheets

BONE FIXATION PLATE SYSTEM AND METHOD

FIELD OF THE INVENTION

The invention relates to a bone fixation system and method.

BACKGROUND OF THE INVENTION

Bones may be reinforced with rigid structures, for example plates, having apertures through which bone screws may pass. Such reinforcing is useful for addressing fractures or other trauma, correcting alignment, or treating disease. A bone plate is used to span a fracture, or to join different bones. It is important that a bone screw securing a bone plate does not loosen and separate from the plate postoperatively. This separation or backing out is typically a result of the failure to achieve sufficient screw thread purchase in the bone, although stripping of the screws has also been known to cause this problem. Regardless of the cause of the hardware failures, a surgeon must repair or replace the broken parts, requiring an undesirable invasive procedure.

Devices for preventing this separation may be associated with the plate and/or screw. Examples include a cover positioned over all or part of the screw head, or an expansion-head screw.

SUMMARY OF THE INVENTION

The present invention relates to a bone plate fixation system that comprises a bone plate having an upper surface, a bone-contacting surface, and a hole defined by a wall and passing through the upper and bone-contacting surfaces; a locking disc inserted into the hole and engaging at least a portion of the wall of the hole; and a bone screw for fixing the bone plate with respect to a bone. The bone screw is insertable through the hole into bone in an insertion direction to fix the bone plate to the bone and the locking disc is operatively associated with the wall to resist resilient deflection of the locking disc in the insertion direction of the bone screw less than the locking disc resists resilient deflection of the locking disc in a direction opposite the insertion direction.

The wall of the bone plate hole can have a groove configured and dimensioned to receive the locking disc. The locking disc can be cooperatively received in the groove such that the groove permits resilient deflection of the locking disc in only the insertion direction of the bone screw.

The plate hole can be provided with an entrance near the upper surface of the bone plate that is chamfered to facilitate insertion of the bone screw. The plate hole can also be provided with an exit near the bone-contacting surface, with a spherical portion extending upward from the exit toward entrance. In one embodiment, the plate hole flares outward from the spherical portion to the groove. The lower portion of the groove can be a tapered section that creates a gap between an inferior aspect of the locking disc and the groove, thereby allowing resilient deflection of the locking disc. A superior aspect of the locking disc can be flush with an upper portion of the groove, thereby inhibiting resilient deflection of the locking disc.

The present invention also relates to a bone plate fixation system that comprises a bone plate having an upper surface, a bone-contacting surface, and a hole defined by a wall and passing through the upper and bone-contacting surfaces, with the wall including a track. A locking cap having a first tab is insertable in the track in an insertion position in which the locking cap can be inserted in a vertical direction into the track and movable to a locked position in which the locking cap is substantially fixed with respect to the track in the vertical direction to inhibit back out of a bone screw inserted in the plate hole.

The bone plate can include a first slot that extends from the upper bone-contacting surface to the track, with the first slot configured and dimensioned to receive the first tab such that the locking cap can be moved from a location external to the bone plate into the track in the insertion position. The locking cap can include a central aperture, the central aperture allowing access to at least a portion of a head of a bone screw inserted or being inserted in the plate hole. In an exemplary embodiment, the central aperture is configured and dimensioned to receive a tool, the tool operative to move the locking cap between the insertion and locked positions.

The locking cap can have an inferior surface that includes a chamfer that allows angulation of a screw inserted into the plate hole at an angle, including an angle other than perpendicular with respect to the bone plate. The track can extend completely around the wall or only partially around the wall, in two or more discrete portions.

The first tab can be operatively received in the track such that when the locking cap is moved to the locked position, at least one of tactile, auditory, and visual feedback is provided to indicate that the locking cap is in the locked position. In this regard, the track can include a protrusion and the first tab can include a recess, with the protrusion engaging the recess when the locking cap is moved to the locked position to provide tactile feedback that the locking cap is in the locked position.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

In the description which follows, any reference to direction or orientation is intended primarily and solely for purposes of illustration and is not intended in any way as a limitation to the scope of the present invention. Also, the particular embodiments described herein are not to be considered as limiting of the present invention.

Fixation systems are disclosed, advantageously utilized with an implant, for example a joining member such as a plate having a fastener or screw hole, though which an anchor portion of a fastener may pass, but not the fastener head. A locking mechanism inhibits the fastener from coming out of the joining member. The implant may have any shape or purpose, and may include, for example, plates, rods, bars, joint replacements, or other anchoring members, and may be used to join body tissues anywhere in the body.

The term "backing out" or "back out" herein refers to movement of a fastener of the disclosure from a position inserted within body tissue, along a direction reversed with respect to a direction of insertion, whereupon the fastener may be caused to exhibit a reduced fastening effect. Back out may be caused by micromotion, disease including tissue degradation, trauma, or other causes.

Clinical applications for the instant disclosure include, but are not limited to, stabilizing any vertebrae, for example cervical, thoracic, lumbar, or sacral vertebrae; joining bone fractures; joining soft tissue, for example tendons or ligaments, to bone; or any procedure hereinafter developed, which advantageously benefits from a reliable anchor connection, and particularly for a screw anchor connection.

Figure 1:
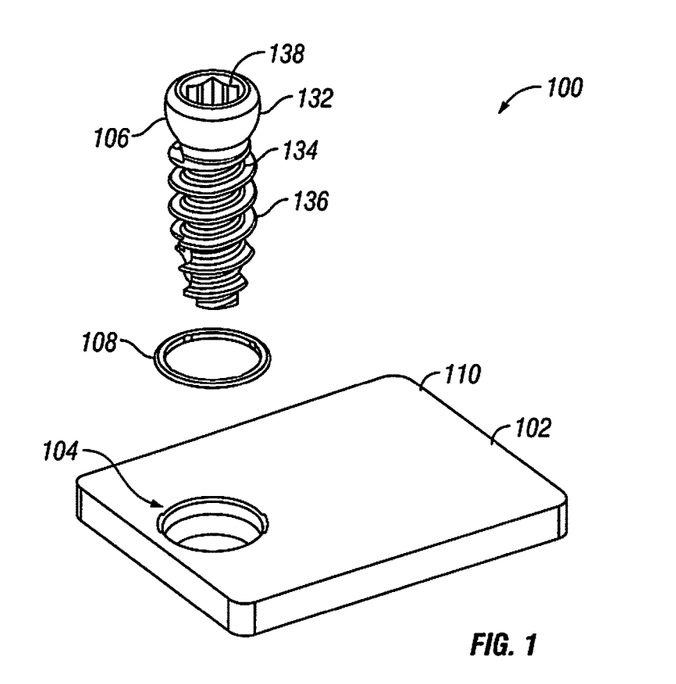
FIG. 1 depicts a perspective exploded view of an embodiment of the bone fixation plate system according to the present invention.

Turning now to the drawings, in which like reference numerals refer to like elements, FIG. 1 shows one embodiment of a bone fixation plate system 100 including a bone plate 102 having a plate hole 104 for receiving a fastener or bone screw 106 which engages body tissue, typically bone, to thereby fix bone plate 102 to the bone tissue. A locking disc 108 is located in hole 104, with bone screw 106 insertable through hole 104 into bone in an insertion direction to fix bone plate 102 to the bone. As set forth in more detail below, locking disc 108 is operatively associated with plate hole 104 to resist resilient deflection in the insertion direction of bone screw 106 less than locking disc 108 resists resilient deflection in a direction opposite the insertion direction to thereby inhibit back out of bone screw 106.

FIG. 1 shows bone plate 102 having a generic configuration. The present invention contemplates that bone plate 102 can be provided with a configuration suitable for a particular clinical application. For example, if bone plate fixation system 100 is to be used in the cervical spine, bone plate 102 can have a configuration like the plates disclosed in U.S. Pat. No. 7,963,981, the content of which is incorporated herein by reference.

Although only one bone plate screw hole 104 is shown, bone plate 102 can be provided with any number of plate holes to suit the intended clinical application, with each plate hole capable of receiving a bone screw. In this regard, the plate hole can be provided with or without a locking disc 108. In other words, the present invention contemplates a bone plate having one or more bone plate screw holes, with one or more of the plate holes provided with a locking disc to inhibit screw back out.

Figure 2:
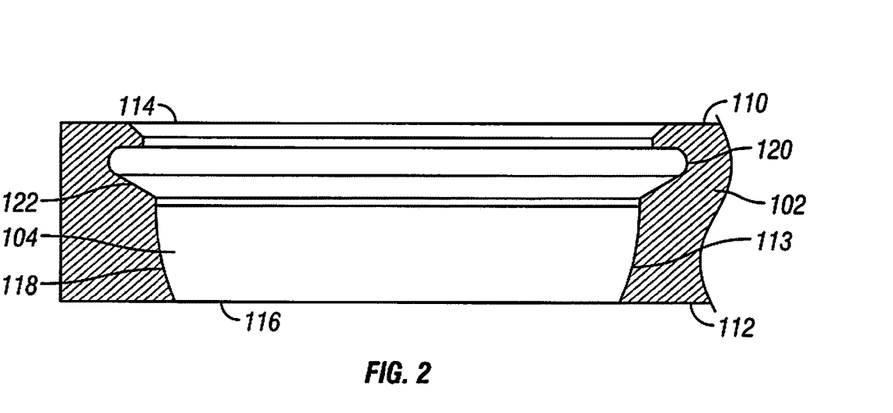
FIG. 2 shows a cross sectional view of the bone screw hole of FIG. 1.

Bone plate 102 has an upper surface 110 and an opposite bone-contacting surface 112, which in use contacts bone or other body tissue to which bone plate 102 is to be fixed. Bone plate screw hole 104 passes through upper 110 and bone-contacting 112 surfaces. As shown in FIG. 2, bone plate screw hole 104 is defined by a wall or periphery and has an entrance 114 that can be advantageously chamfered to facilitate insertion of bone screw 106. Plate hole 104 additionally includes a reduced dimension located on an opposite end to entrance 114, at an exit 116, operative (in conjunction with the configuration and dimensions of the rest of plate hole 104 relative to the configuration and dimensions of bone screw 106) to limit the extent bone screw 106 is insertable into plate hole 104.

Plate hole 104 has a spherical portion 118 extending upward from exit 116 toward entrance 114. As set forth in more detail below, preferably the spherical portion may accommodate a bone screw having a spherical head. However, the present invention is not limited to spherical curvatures or spherical heads. In other embodiments, any complementary head and receptacle may be used. Plate hole 104 flares outward from spherical portion 118 to a groove 120 which is configured and dimensioned to receive locking disc 108. The outward flaring provides the lower portion of groove 120 with a tapered section 122.

Figure 3:
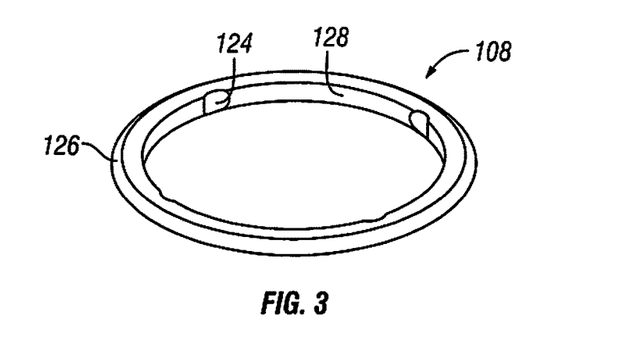
FIG. 3 shows a perspective view of the locking disc of FIG. 1.

FIG. 3 shows locking disc 108 is shaped like an o-ring. The inner surface can be provided with one or more cutouts 124 to facilitate insertion and removal of locking disc 108. Advantageously, the cutouts 124 provide flexibility to the locking disc 108, and in particular, allow the locking disc 108 to flex downward toward bone but not upwards. As shown in FIG. 3, the locking disc 108 includes four cutouts 124 distributed at equal distances from each other around the locking disc 108. In this regard, locking disc 108 can be provided pre-assembled in plate hole 104 or the surgeon can insert locking disc 108 into plate hole 104. Either way, the surgeon can selectively insert or remove locking disc 108 from a given plate hole 104. Although locking disc 108 is shown as forming a complete circle, locking disc 108 need not extend a full 360°, so that only a portion of a circle is formed. An outer surface 126 of locking disc 108 can be curved to mate with groove 120. When bone screw 106 has a spherical head, an inner surface 128 can also be curved to facilitate insertion of bone screw 106.

Figure 4:
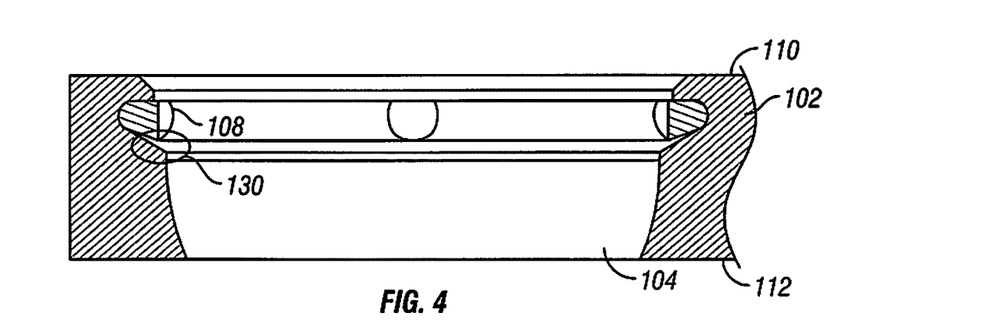
FIG. 4 shows a cross sectional view of the locking disc and bone screw hole with the bone screw not inserted.

As shown in FIG. 4, when locking disc 108 is inserted in plate hole 104, locking disc 108 fits snugly in groove 120. In the superior aspect, there is little or no space between groove 120 and locking disc 108. This minimizes or reduces resilient upward deflection of locking disc 108 to inhibit screw back out. In the inferior aspect, tapered section 122 of groove 120 results in a space or gap 130, which provides for downward resilient deflection of locking disc 108 as bone screw 106 is being inserted into plate hole 104. Thus, advantageously, screw 106 can be inserted downwardly by overcoming the resilient force of the locking disc 108, but will have sufficient counterforces to prevent back out of the screw 106 once it is inserted.

Figure 5:
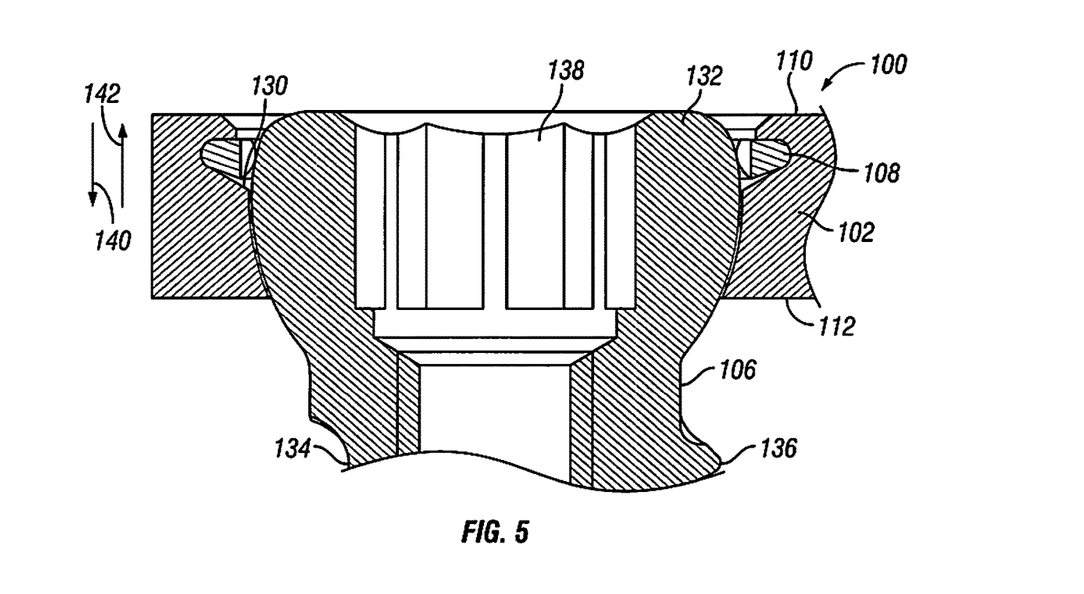
FIG. 5 shows a cross sectional view of the locking disc and bone screw hole with the bone screw fully seated in the bone screw hole.

FIGS. 1 and 5 show bone screw 106 has a head portion 132 and a shaft portion 134 and may be passed into a preformed opening in body tissue, or may form or expand an opening in body tissue by self drilling and/or self tapping. At least a portion of shaft 134 is provided with a thread or threads 136 to engage body tissue, for example cortical bone, cancellous bone, tendinous, ligamentous, or other body tissue capable of being securely engaged by threads. Head 132 is provided with tool engagement means, for example a Phillips, hex, or other engagement profile 138, whereby a tool may be used to position and or drive screw 106 into engagement with bone plate 102 and into body tissue. Although head 132 is shown as a spherical head, the present invention is not limited to spherical curvatures or spherical heads as previously noted. In other embodiments, any complementary head and receptacle may be used.

Bone plate 102 and bone screw 106 may be comprised of any material, such as a metal, alloy, or any combination of the two. The material used is preferably bio-compatible and capable of withstanding the conditions of a body over a desired period of time. In some embodiments, this is achieved by manufacturing plate 102 and screw 106 using a metallic material such as titanium or stainless steel. Titanium has sufficient ductility to permit a desired amount of curving of plate 102 if need be (e.g. to conform to the shape of the vertebrae) yet has the strength to maintain its structural integrity.

Locking disc 108 may be comprised of any material, such as a metal, polymer, composite, or any combination of the three. The material used is preferably bio-compatible and capable of withstanding the conditions of a body over a desired period of time. In some embodiments, this is achieved by manufacturing locking disc 108 using material such as titanium or any medical grade polymer.

Referring principally to FIG. 5, in use screw 106 is inserted into plate hole 104 in an insertion direction 140. As a result of the resiliency of locking disc 108 and space or gap 130, locking disc flexes downward (i.e. in insertion direction 140) as bone screw 106 is being inserted into plate hole 104. In the embodiment shown, there is preferably an increase in resistance to resilient deflection of locking disc 108 as bone screw 106 is being inserted into plate hole 104 until the largest diameter of the generally spherically shaped head 132 of bone screw 106 contacts locking disc 108. Once the largest diameter of head 132 reaches locking disc 108, the resistance to downward deflection of locking disc 108 begins to decrease. This change in resistance advantageously provides tactile feedback to the surgeon that bone screw 106 is sufficiently seated. Visual feedback can also be provided in that it will be evident when bone screw 106 is above locking disc 108 and is therefore not sufficiently seated.

As a result of the snug fit in the superior aspect of locking disc 108 into groove 120, resilient upward deflection of locking disc 108 is minimized or reduced to inhibit screw back out in an opposite direction 142 with respect to insertion direction 140. Screw 106 may be screwed into bony tissue at any desired angle. In other words, screw 106 does not have to be inserted perpendicular to plate 102.

FIGS. 6-16 show another embodiment of a bone plate system 200 according to the present invention, which, as set forth in more detail below, can provide tactile, visual, and/or other feedback to the surgeon that a locking mechanism is engaged to inhibit back out of a bone screw.

Figure 6:
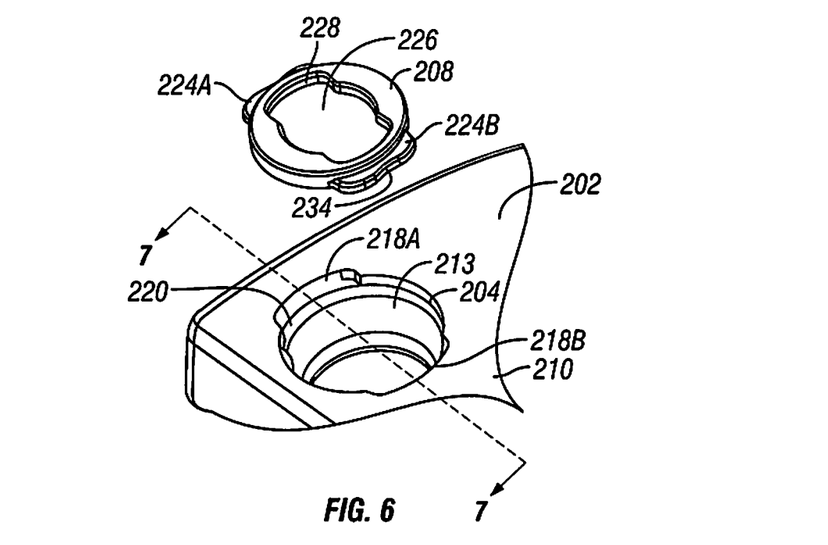
FIG. 6 is a perspective view of another embodiment of the bone fixation plate system according to the present invention, showing a portion of a bone plate and a locking cap prior to insertion.
Figure 7:
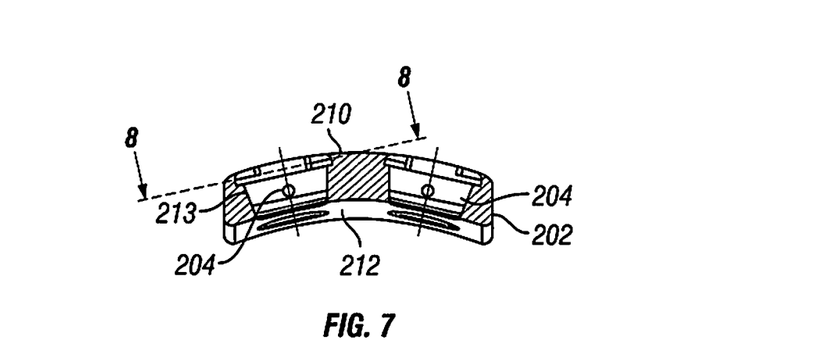
FIG. 7 shows a cross sectional view of the bone plate of FIG. 6 through line 7-7.
Figure 8:
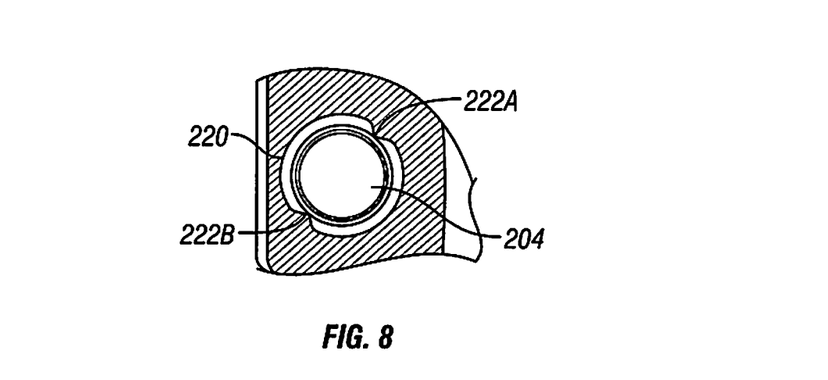
FIG. 8 shows a cross sectional view of the bone plate of FIG. 6 through line 8-8.

As shown in FIGS. 6-8, bone fixation plate system 200 includes a bone plate 202 having a plate hole 204 for receiving a fastener or bone screw 206 (FIG. 16) which engages body tissue, typically bone, to thereby fix bone plate 202 to the bone tissue. A locking cap 208 is located in hole 204, with bone screw 206 insertable through hole 204 into bone in an insertion direction to fix bone plate 202 to the bone. As set forth in more detail below, locking cap 208 is inserted into screw hole 204 and then moved to a locked position in which locking cap is substantially fixed with respect to screw hole 204 to inhibit back of a bone screw inserted in plate hole 204.

Bone plate 202, like bone plate 102, can be provided with a configuration suitable for a particular clinical application. Although only two bone plate screw holes 204 are shown, bone plate 202 can be provided with any number of plate holes to suit the intended clinical application, with each plate hole capable of receiving a bone screw. In this regard, the plate hole can be provided with or without a locking cap 208. In other words, the present invention contemplates a bone plate having one or more bone plate screw holes, with one or more of the plate holes provided with a locking cap to inhibit screw back out.

Bone plate 202 has an upper surface 210 and an opposite bone-contacting surface 212, which in use contacts bone or other body tissue to which bone plate 202 is to be fixed. Bone plate screw hole 204 passes through upper 210 and bone-contacting 212 surfaces. Bone plate screw hole 204 is defined by a wall or periphery 213 and has an entrance 214 that can be advantageously chamfered to facilitate insertion of bone screw 206. Plate hole 204 additionally includes a reduced dimension located on an opposite end to entrance 214, at an exit 216, operative (in conjunction with the configuration and dimensions of the rest of plate hole 204 relative to the configuration and dimensions of bone screw 206) to limit the extent bone screw 206 is insertable into plate hole 204. In this regard, plate hole 204 can have a spherical configuration extending upward from exit 216 toward entrance 214. Preferably the spherical portion may accommodate a bone screw having a spherical head. However, the present invention is not limited to spherical curvatures or spherical heads. In other embodiments, any complementary head and receptacle may be used.

A first slot 218a and a second slot 218b extend from upper surface 210 to a track 220 located on wall 213 of plate hole 204. Slots 218a and 218b allow locking cap 208 to be inserted into plate hole 204. Although two slots are shown, the number and shape of slots 218a and 218b can be selected based on the configuration of locking cap 208. Although track 220 is shown as extending completely (i.e. 360°) around wall 213, track can extend only partially around wall 213. In an exemplary embodiment, track 220 comprises two discrete portions with first slot 218a providing access to the first portion of track 220 and second slot 218b providing access to the second portion of track 220. As best seen in FIG. 8, track 220 has a first protrusion 222a and a second protrusion 222b, which will be described below in further detail.

Referring now primarily to FIGS. 9-12, locking cap 208 has a first tab 224a and a second tab 224b. First tab 224a is insertable in track 220 (via either one of first and second slots 218a, 218b) in an insertion position in which locking cap 208 can be inserted in a vertical direction into track 220 and movable to a locked position in which locking cap 208 is substantially fixed with respect to track 220 in the vertical direction to inhibit back out of a bone screw inserted in plate hole 204. Similarly, second tab 224a is insertable in track 220 (via the other of first and second slots 218a, 218b) in an insertion position in which locking cap 208 can be inserted in a vertical direction into track 220 and movable to a locked position in which locking cap 208 is substantially fixed with respect to track 220 in the vertical direction to inhibit back out of a bone screw inserted in plate hole 204. In some embodiments, the first slot 218a and second slot 218b are configured differently such that first tab 224a is configured to fit in first slot 218a, while second tab 224b is configured to fit in second slot 218b. In other embodiments, first tab and second tab 224a and 224b can fit in either of first slot and second slot 218a and 218b.

Figure 11:
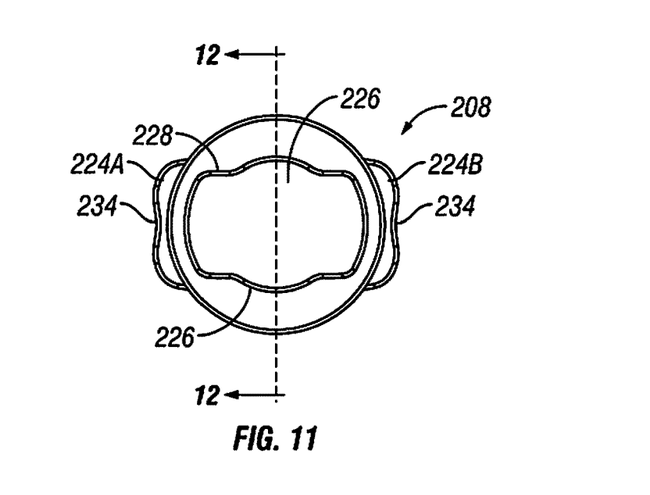
FIG. 11 shows a top view of the locking cap.
Figure 12:
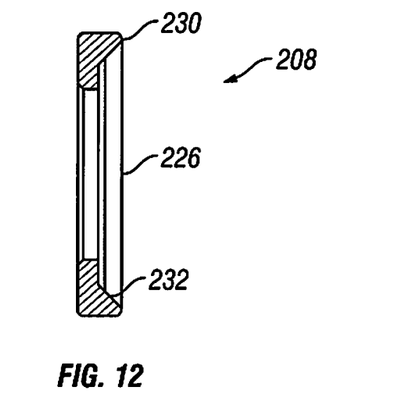
FIG. 12 shows a cross sectional view of the locking cap through line 11-11.

Locking cap 208 can include a central aperture 226 that allows access to at least a portion of a head of a bone screw inserted or being inserted in plate hole 204. This provides for adjustment of screw insertion even with locking cap 208 positioned in plate hole 204. Central aperture 226 can be configured and dimensioned to receive a tool operative to move locking cap 208 between the insertion and locked positions. In this regard, FIG. 11 shows central aperture 226 with wings 228 engageable by a tool such as a slotted screwdriver for rotating or twisting locking cap 208 into or out of the insertion and locked positions. Other configurations are contemplated by the present invention.

Figure 9A:
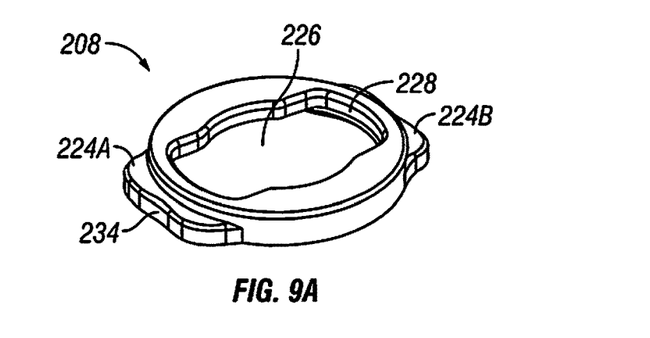
FIGS. 9A and 9B show perspective views of the top and bottom of the locking cap of FIG. 6.
Figure 9B:
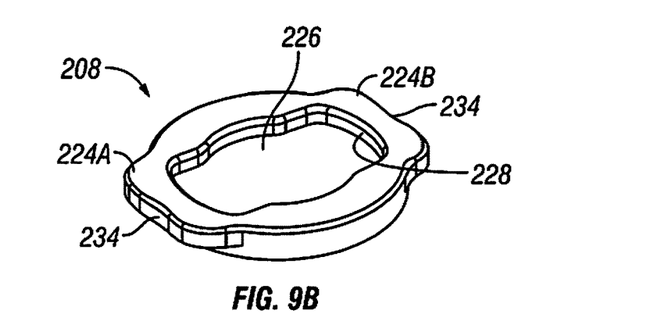
Figure 10:
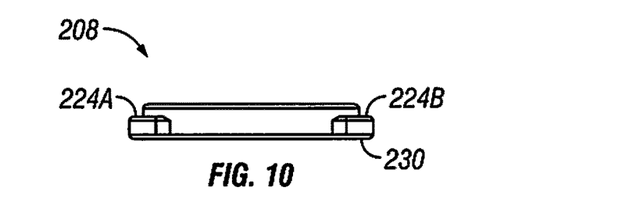
FIG. 10 shows a side view of the locking cap.

As was the case for bone plate 102, a bone screw may be screwed into bony tissue at any desired angle. In other words, the bone screw does not have to be inserted perpendicular to plate 202. Locking cap 208 can have an inferior surface 230 that includes a chamfer 232 to accommodate angulation of a screw inserted into plate hole 204 at an angle other than perpendicular with respect to bone plate 202.

One or both tabs 224a, 224b can have a recess 234, which cooperates with protrusions 222a, 222b to provide tactile feedback that locking cap 208 is in the locked position. In particular, as locking cap 208 is rotated from the insertion position, recess 234 on one of tabs 224a, 224b engages one of protrusion 222a, 222b in track 220. The change in resistance to rotation provides tactile feedback that locking cap 208 is in the locked position. The engagement of recess 234 with protrusion 222a or protrusion 222b can also reduce the possibility that locking cap 208 unintentionally moves from the locked position to the insertion position, thereby further inhibiting back out of a bone screw.

Figure 13:
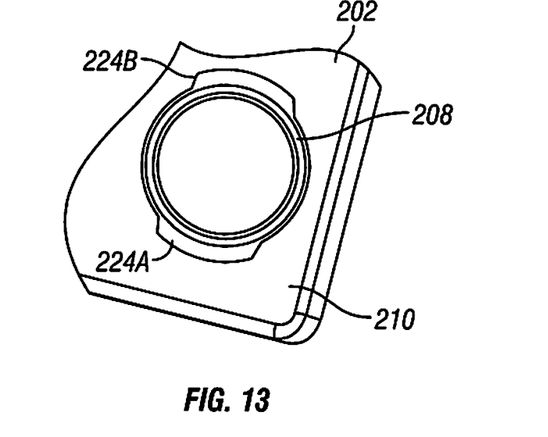
FIG. 13 shows the locking cap inserted in a plate hole.
Figure 14:
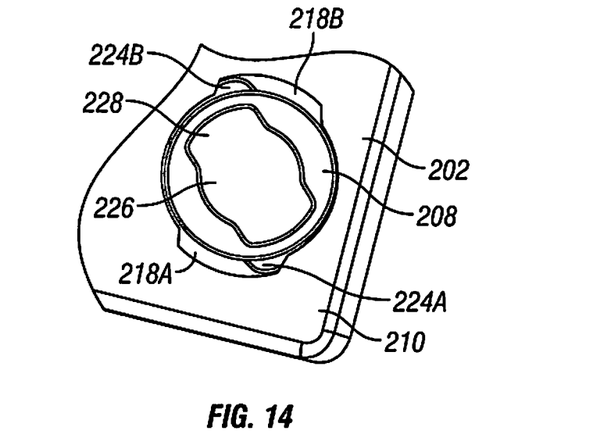
FIG. 14 shows the locking cap inserted in the plate hole rotated to a partial locked position.
Figure 15:
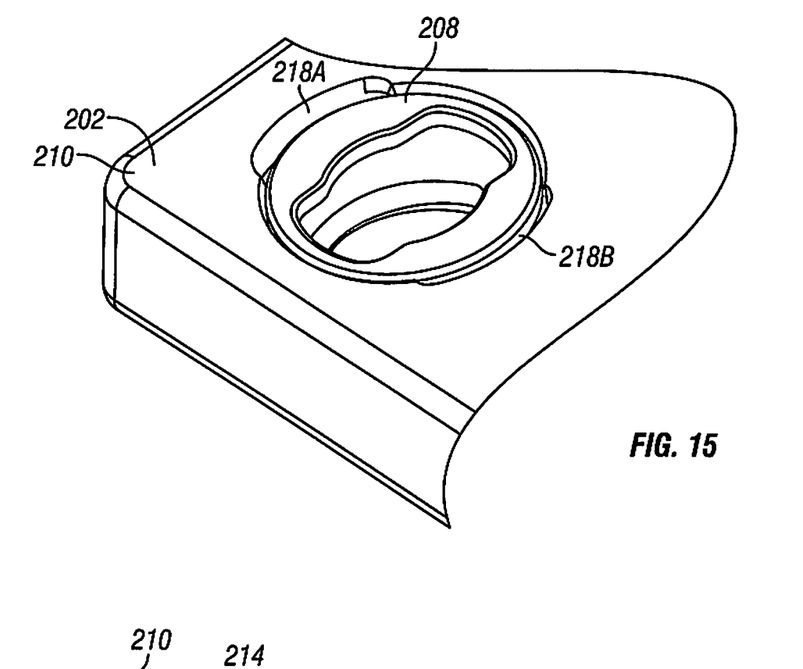
FIG. 15 shows the locking cap inserted in the plate hole rotated to a locked position.

The cooperation of locking cap 208 and plate hole 204 will be discussed further with reference to FIGS. 13-15, which have the bone screw omitted for simplicity. As shown in FIG. 13, tab 224a is aligned with slot 218a and tab 224b is aligned with slot 218b when locking cap 208 is in the insertion position. Because of this alignment, locking cap 208 can be inserted in a vertical direction into track 220. In FIG. 14, locking cap 208 is rotated in track 220 so that a portion of tab 224a is no longer aligned with slot 218a and a portion of tab 224b is no longer aligned with slot 218b. As a result, locking cap 208 is substantially confined in the vertical direction thereby limiting back out of a bone screw inserted in plate hole 204.

As locking cap 208 is further rotated in track 220, recess 234 on tab 224a engages protrusion 222a and recess 234 on tab 224b engages protrusion 222b, providing tactile feedback that locking cap 208 is in the locked position. The engagement of tabs 224, 224b with recesses 234 may also provide audible feedback. In addition to, or in lieu of tactile and/or audible feedback, visual feedback can be provided to confirm locking cap 208 is in the locked position. An example of visual feedback is shown in FIG. 15 in which wings 228 on locking cap 208 are positioned approximately 90° from slots 218a, 218b. Locking cap 208 and/or bone plate 202 can be provided with other indicia, such as etching or other markings, to indicate the insertion and/or locked positions.

As previously noted, the number of tabs of locking cap 208 is not limited to two and bone plate hole 204 can be provided with a corresponding number of slots. In this regard, the present invention contemplates that bone plate hole 204 is provided with more slots than locking cap 208 is provided with tabs. As shown in the figures, locking cap 208 can rotate in either direction within track 220 between the insertion position and the locked position. However, locking cap 208 and/or track 220 can be configured and dimensioned and arranged so that rotation in one direction is needed to move from the insertion position to the locked position and rotation in the opposite direction is needed to move from the locked position to the insertion position.

Figure 16:
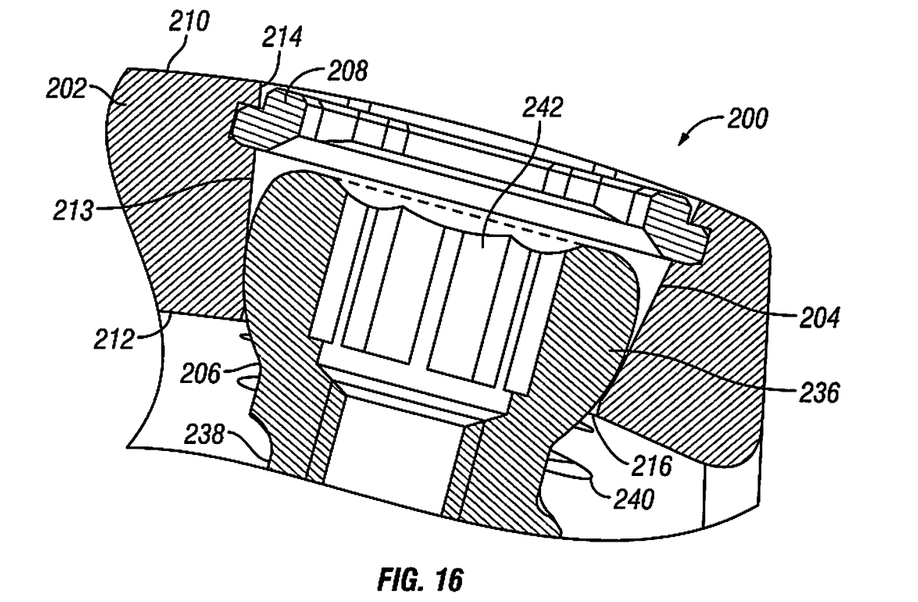
FIG. 16 shows a cross sectional view of a bone screw in the plate hole with the locking cap.

FIG. 16 shows bone screw 206 seated in plate hole 204 with locking cap 208 inhibiting back out of bone screw 206 by physically blocking or otherwise interfering with backward movement of bone screw 206. Bone screw 206 can be substantially similar to, if not identical to, bone screw 106. Accordingly, reference is made to the description of bone screw 106. Bone screw 206 has a head portion 236 and a shaft portion 238 and may be passed into a preformed opening in body tissue, or may form or expand an opening in body tissue by self drilling and/or self tapping. At least a portion of shaft 238 is provided with a thread or threads 240 to engage body tissue, for example cortical bone, cancellous bone, tendinous, ligamentous, or other body tissue capable of being securely engaged by threads. Head 236 is provided with tool engagement means, for example a Phillips, hex, or other engagement profile 242, whereby a tool may be used to position and or drive screw 206 into engagement with bone plate 202 and into body tissue. Although head 236 is shown as a spherical head, the present invention is not limited to spherical curvatures or spherical heads as previously noted. In other embodiments, any complementary head and receptacle may be used.

Bone plate 204, bone screw 206, and locking cap 208 may be comprised of any material, such as a metal, alloy, or any combination of the two. The material used is preferably bio-compatible and capable of withstanding the conditions of a body over a desired period of time. In some embodiments, this is achieved by manufacturing plate 202, screw 206, and locking cap 208 using a metallic material such as titanium or stainless steel. Titanium has sufficient ductility to permit a desired amount of curving of plate 202 if need be (e.g. to conform to the shape of the vertebrae) yet has the strength to maintain its structural integrity.

In use, bone plate 202 is positioned in a therapeutic location in the body, and body tissue is approximated or otherwise positioned to be stabilized. Bone screw 206 may be positioned through plate hole 204 before or after connecting a tool, after which the tool is used to engage bone screw 206 with body tissue. Once bone screw 206 has been inserted sufficiently through plate hole 204 so that head portion 236 of bone screw 206 is below track 220, locking cap 208 can be positioned in track 220 if desired and if tool is configured to pass through central aperture 226 of locking cap 208 to allow further tightening. Locking cap 208 can remain in the insertion position or could be moved to the locked position or a position therebetween. Seating of the bone screw 206 is then completely and if not previously done so, locking cap 208 is moved to the locked position. Alternatively, bone screw 206 can be fully seated in plate hole 204 before locking cap 208 is positioned in track 220 and moved to the locked position. Either way, a tool that is configured and dimensioned to allow adjustment of the seating of bone screw 206 with locking cap 208 in position is preferably used.

It will be appreciated by persons skilled in the art that the present invention is not limited to what has been particularly shown and described herein above. All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A bone plate fixation system comprising:
    a bone plate having an upper surface, a bone-contacting surface, and a hole defined by a wall and passing through the upper and bone-contacting surfaces;
    a locking ring inserted into the hole and engaging at least a portion of the wall of the hole; and
    a bone screw for fixing the bone plate with respect to a bone, the bone screw having a head and a shaft with a thread for engaging bone, wherein the locking ring is independent from the bone screw such that it can be inserted into the hole of the bone plate without the bone screw, the locking ring forms a complete circle having an inner surface configured to be in contact with the bone screw, an outer surface configured to be in contact with the bone plate, an upper surface and a lower surface defining a width therebetween,
    wherein the bone screw is insertable through the hole into bone in an insertion direction to fix the bone plate to the bone and wherein the locking ring is operatively associated with the wall to resist resilient deflection of the locking ring in the insertion direction of the bone screw less than the locking ring resists resilient deflection of the locking ring in a direction opposite the insertion direction,
    wherein the locking ring is positioned entirely between the upper surface and the bone-contacting surface,
    wherein the locking ring has a thickness extending from the inner surface to the outer surface and at least one cutout on the inner surface extending from the upper surface to the lower surface of the locking ring, the cutout extending from the inner surface to a distance less than the thickness of the locking ring and a having a depth, the width of the locking ring being greater than the depth of the cutout, and
    wherein the locking ring engages an outer spherical portion of the head of the bone screw.

2. The bone fixation system of claim 1, wherein the wall of the bone plate hole has a groove configured and dimensioned to receive the locking ring.

3. The bone fixation system of claim 2, wherein the locking ring is cooperatively received in the groove such that the locking ring resists resilient deflection of the locking ring in the insertion direction of the bone screw less than the locking ring resists resilient deflection of the locking ring in a direction opposite the insertion direction.

4. The bone fixation system of claim 3, wherein the locking ring is cooperatively received in the groove such that the groove permits resilient deflection of the locking ring in only the insertion direction of the bone screw.

5. The bone fixation system of claim 3, wherein the plate hole has an entrance near the upper surface of the bone plate and wherein the plate hole is chamfered to facilitate insertion of the bone screw.

6. The bone fixation system of claim 5, wherein the plate hole has an exit near the bone contacting surface and wherein the plate hole has a spherical portion extending upward from the exit toward the entrance.

7. The bone fixation system of claim 6, wherein the plate hole flares outward from the spherical portion to the groove.

8. The bone fixation system of claim 7, wherein a lower portion of the groove has a tapered section, the tapered section creating a gap between an inferior aspect of the locking ring and the groove, thereby allowing resilient deflection of the locking ring.

9. The bone fixation system of claim 8, wherein a superior aspect of the locking ring is flush with an upper portion of the groove, thereby inhibiting resilient deflection of the locking ring.

10. The bone fixation system of claim 1, wherein the at least one cutout includes four cutouts distributed at equal distances from each other around the locking ring.

11. A method of securing body tissue, the method comprising:
    providing the bone plate fixation system of claim 1;
    passing the shaft of the bone screw through the plate hole in an insertion direction; and
    attaching the bone screw shaft to body tissue by further passing the bone screw shaft through the plate hole in the insertion direction, wherein the locking ring is operatively associated with the wall to resist resilient deflection of the locking ring in the insertion direction of the bone screw less than the locking ring resists resilient deflection of the locking ring in a direction opposite the insertion direction.

* * * * *